United States Patent
Yang et al.

(10) Patent No.: US 11,591,646 B2
(45) Date of Patent: Feb. 28, 2023

(54) SMALL RNA DETECTION METHOD BASED ON SMALL RNA PRIMED XENOSENSOR MODULE AMPLIFICATION

(71) Applicant: XENOHELIX CO., LTD, Jeonju-si (KR)

(72) Inventors: Seong Wook Yang, Seoul (KR); Seok Keun Cho, Goyang-si (KR); Pratik Shah, Seoul (KR); Riddhi Nitin Nagda, Seoul (KR)

(73) Assignee: XENOHELTX CO., LTD, Jeonju-si (KR)

( * ) Notice: Subject to any disclaimer, the term of this patent is extended or adjusted under 35 U.S.C. 154(b) by 66 days.

(21) Appl. No.: 17/038,412

(22) Filed: Sep. 30, 2020

(65) Prior Publication Data
US 2021/0017580 A1  Jan. 21, 2021

Related U.S. Application Data

(63) Continuation of application No. PCT/KR2019/014837, filed on Nov. 4, 2019.

(30) Foreign Application Priority Data

Apr. 19, 2019 (KR) .................. 10-2019-0046388
Jul. 25, 2019 (KR) .................. 10-2019-0090404

(51) Int. Cl.
*C12Q 1/686* (2018.01)
*C12Q 1/6876* (2018.01)

(52) U.S. Cl.
CPC ........... *C12Q 1/686* (2013.01); *C12Q 1/6876* (2013.01); *C12Q 2521/301* (2013.01); *C12Q 2525/113* (2013.01); *C12Q 2525/121* (2013.01); *C12Q 2525/179* (2013.01); *C12Q 2525/185* (2013.01); *C12Q 2525/207* (2013.01); *C12Q 2537/149* (2013.01); *C12Q 2565/537* (2013.01); *C12Q 2600/178* (2013.01)

(58) Field of Classification Search
CPC .............. C12Q 1/686; C12Q 2521/301; C12Q 2525/113; C12Q 2525/121; C12Q 2525/179; C12Q 2525/185; C12Q 2525/207; C12Q 2537/149; C12Q 2565/537; C12Q 1/6825; C12Q 2525/204; C12Q 2531/113
See application file for complete search history.

(56) References Cited

U.S. PATENT DOCUMENTS

| | | | |
|---|---|---|---|
| 2005/0272075 A1* | 12/2005 | Jacobsen | C12Q 1/6809 435/6.1 |
| 2006/0172333 A1* | 8/2006 | Chen | C12Q 1/6869 435/6.12 |
| 2007/0077582 A1 | 4/2007 | Slepnev | |
| 2011/0294689 A1* | 12/2011 | Namsaraev | C12Q 1/6816 506/26 |
| 2014/0221228 A1 | 8/2014 | Ginsberg et al. | |

FOREIGN PATENT DOCUMENTS

| | | |
|---|---|---|
| KR | 10-2012-0097793 A | 9/2012 |
| WO | 2016/134258 A1 | 8/2016 |

OTHER PUBLICATIONS

Dong et al. Utilizing RNA/DNA hybridization to directly quantify mRNA levels in microbial fermentation samples. Journal of Microbiological Methods 2009; 79: 205-210 (Year: 2009).*
Nichols et al. Ribonucleases. Current Protocols in Molecular Biology 2008; 3.13.1-3.13.8 (Year: 2008).*
A. Kalota et al., "2'-Deoxy-2,-fluoro-β-D-arabinonucleic acid (2'F-ANA) modified oligonucleotides (ON) effect highly efficient, and persistent, gene silencing", Nucleic Acids Research, 2006, pp. 451-461, vol. 34, No. 2.
International Search Report for PCT/KR2019/014837 dated, Mar. 9, 2020.

\* cited by examiner

*Primary Examiner* — Angela M. Bertagna
(74) *Attorney, Agent, or Firm* — Sughrue Mion, PLLC

(57) ABSTRACT

The present invention may provide a small RNA detection sensor comprising: at one end thereof, a first sensing region comprising nucleotides having a sequence complementary to target small RNA; and a PCR-capable region that is coupled to the first sensing region, the small RNA detection sensor to synthesize a replication region complementary to the PCR-capable region by a DNA polymerase by using the target small RNA as a primer, and amplify the PCR-capable region and the replication region.

5 Claims, 10 Drawing Sheets

Specification includes a Sequence Listing.

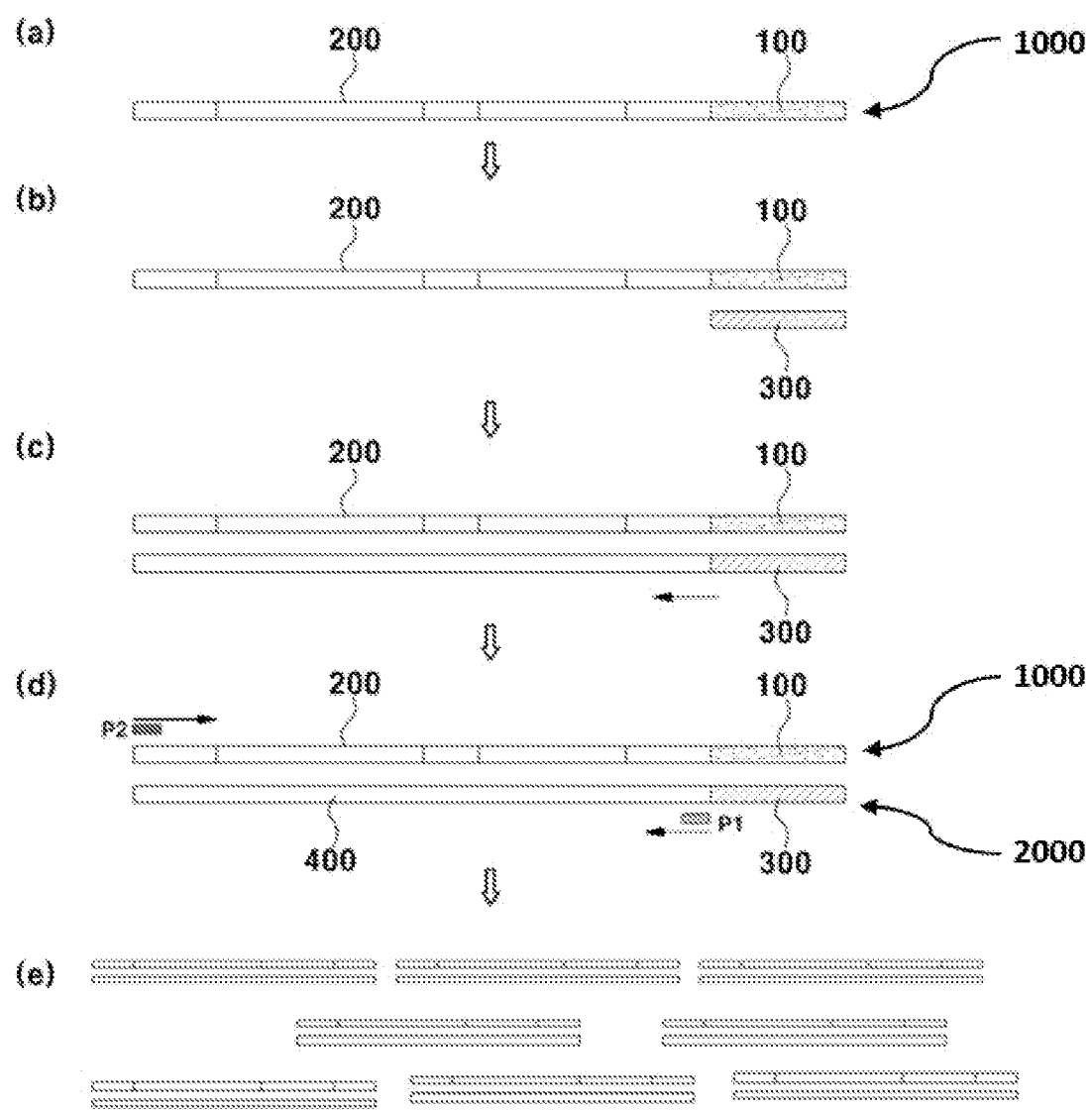

FIG. 3A

>SenR210
AATGATACGGCGACCACCGAGATCTACACGTTCAGAGTTCTACAGTCCGACGATCTGGAATTCTCGGGTGCCAAGGA
ACTCCAGTCACATCACGATCTCGTATGCCGTCTTCTGCTTGT CAG CCG CTG TCA CAC GCA CAG-amine (index 2)
         ▲                                                            ▲
    Ana modification                                             Ana modification

FIG. 3B

>SenR21
AATGATACGGCGACCACCGAGATCTACACGTTCAGAGTTCTACAGTCCGACGATCTGGAATTCTCGGGTGCCAAGGA
ACTCCAGTCACCGTGAATCTCGTATGCCGTCTTCTGCTTGT CAA CAT CAG TCT GAT AAG CTA-amine (index 1)
         ▲                                                            ▲
    Ana modification                                             Ana modification

FIG. 3C

>hsa-miR-210-3p
CUGUGCGUGUGACAGCGGCUGA

FIG. 3D

>hsa-miR-21-5p
UAGCUUAUCAGACUGAUGUUGA

FIG. 8

>SenR210ma
AATGATACGGCGACCACCGAGATCGTACACGTTCAGAGTTCTACAGTCCGACGATCTGGAATTCTCGGGTGCCAAG
GAACTCCAGTCACATCArCrGrATCTCGTATGCCGTCTTCTGCTTGT CAG CCG CTG TCA CAC GCA CArG (index 2)
                 ↑                                                          ↑
            Ana modification                                           Ana modification

SMALL RNA DETECTION METHOD BASED ON SMALL RNA PRIMED XENOSENSOR MODULE AMPLIFICATION

CROSS-REFERENCE TO RELATED APPLICATIONS

This application is a Continuation of PCT International Application No. PCT/KR2019/014837 filed on Nov. 4, 2019, which claims priority under 35 U.S.C. § 119(a) to Korean Patent Application No. 10-2019-0090404 filed on Jul. 25, 2019 and Korean Patent Application No. 10-2019-0046388 filed on Apr. 19, 2019, the entire disclosures of which are incorporated herein by reference.

TECHNICAL FIELD

The present invention relates to a small RNA detection technology, and more particularly to a method and sensor for small RNA detection.

BACKGROUND ART

Small RNAs include microRNA (miRNA), small interfering RNA (siRNA), and Piwi-interacting RNA (piRNA), and these small RNAs regulate gene expression through a mechanism of binding to messenger RNAs (mRNAs), to which small RNAs are complementarily bindable, and cleaving the mRNAs, or inhibiting translation into proteins. Small RNAs are known to play pivotal roles in various biological processes such as cell development and differentiation, programmed cell death, and immune responses, and it is known that the differential expressions of specific small RNAs in cells are associated with various diseases including cancers. Therefore, detecting specific small RNAs with high efficiency is emerging as an essential issue in the fields of medical life research and disease diagnosis.

Existing detection techniques are mainly based on a technique of ligating an adaptor consisting of DNA to the 5' and 3' regions of small RNAs, or ligating poly(A) tail RNA to an adaptor, and then converting the resultant structure into cDNA using reverse transcriptase, followed by polymerase chain reaction (PCR) amplification. In these detection methods, the recognition efficiency of a target is too low in the reverse transcription process, and in many cases, since small RNAs have a short length, inaccurate results are often caused by non-specific primer interactions during PCR-based amplification. Besides, by using detection methods such a nucleic acid amplification reaction, it is generally impossible to directly analyze the nucleotide sequences of amplified nucleic acids after the nucleic acid amplification process and to analyze the nucleotide sequences, an additional library production procedure for sequencing is required.

DESCRIPTION OF EMBODIMENTS

Technical Problem

Therefore, the technical problem to be solved by the present invention is to provide a small RNA detection method capable of recognizing target small RNAs without ligating DNA adaptors to both 5' and 3' regions or using polyA tail RNA as a 3' region adaptor for reverse transcriptase activity.

Also, the technical problem to be solved by the present invention is to provide a small RNA detection sensor capable of maximizing the ability to detect a target, removing non-specific amplification, and performing direct sequencing of an amplified product.

Technical Solution

According to an aspect of the present invention, there is provided a small RNA detection sensor including: at one end thereof, a first sensing region including nucleotides having a sequence complementary to a target small RNA; and a PCR-capable region that is coupled to the first sensing region, the small RNA detection sensor to synthesize a replication region complementary to the PCR-capable region by a DNA polymerase by using the target small RNA as a primer, and amplify the PCR-capable region and the replication region.

The first sensing region may include: at least one amine modification portion that prevents PCR amplification from occurring due to the formation of a non-specific self-dimer with a first sensing region of another detection sensor, and at least one nucleotide substitution portion that is efficiently cleaved by a nuclease.

In one embodiment, the nucleotide substitution portion may include an ANA nucleotide substituted for a nucleotide of the first sensing region. The nucleotide substitution portions may be located at the positions of $88^{th}$ and $138^{th}$ nucleotides from the 5' end of the small RNA detection sensor.

The nucleotide substitution portion may include an RNA nucleotide substituted for a DNA nucleotide of a nucleotide sequence of the short RNA detection sensor.

In one embodiment, a 3' end of the PCR-capable region may be coupled to the first sensing region, and a 5' end of the PCR-capable region may constitute the other end of the sensor.

The PCR-capable region may include a barcode region, the barcode region may include information related to the target small RNA to be detected by the first sensing region, and the barcode region may consist of a set of 9 nucleotide sequences.

The PCR-capable region may include a primer binding region at one or more of both ends thereof, the primer binding region enabling the PCR-capable region to be PCR-amplified.

The PCR-capable region may include at least one amine modification portion for inhibiting the self-amplification of the PCR-capable region.

In one embodiment, the target small RNAs may include miRNAs and small interfering RNAs.

According to another aspect of the present invention, there is provided a small RNA detection method including: providing a sensor including: at one end thereof, a rust sensing region including nucleotides having a sequence complementary to a target small RNA; and a PCR-capable region that is coupled to the first sensing region, wherein the first sensing region includes at least one amine modification portion and at least one nucleotide substitution portion, and the PCR-capable region includes a primer binding region, a barcode region, and a residual nucleotide region; allowing the target small RNA in a test sample to bind to the first sensing region of the sensor; synthesizing a replication region by replicating the PCR-capable region using the bound target small RNA as a primer to form a chimera strand complementary to the sensor adding a nuclease to the sample; binding the nuclease with the nucleotide substitution portion of the first sensing region in the sample that does not form the chimera strand and small RNAs that do not form the chimera strand to cleave non-specific small RNA and a detection sensor including the first sensing region that do not form the chimera strand; removing the cleaved detection sensor and non-specific small RNAs; and PCR-amplifying the PCR-capable region and the replication region using a set of primers specific to the primer binding regions of the sensor and the chimera strand.

The amine modification portion may prevent PCR amplification of a strand produced by self-dimer formation of the first sensing region with a first sensing region of another detection sensor.

The nucleotide substitution portion may include a nucleotide with high sensitivity to a nuclease that cleaves the first sensing region, and may include an ANA nucleotide or an RNA nucleotide.

The nucleotide substitution portions including the ANA nucleotide may be located at the positions of $88^{th}$ and $138^{th}$ nucleotide from the 5' end of the small RNA detection sensor.

The nucleotide substitution portions including the RNA nucleotide may be located at positions of $24^{th}$, $25^{th}$, $26^{th}$, $93^{th}$, $94^{th}$, $95^{th}$, and $140^{th}$ nucleotide from the 5' end of the small RNA detection sensor.

In one embodiment, the target small RNAs may include miRNAs and small interfering RNAs, and the barcode region may consist of a set of 9 nucleotide sequences.

Advantageous Effects of Invention

According to an embodiment of the present invention, a small RNA detection method with high accuracy and a high amplification rate can be provided by using a sensor with a partial region complementary to a target small RNA, and the bound small RNA itself acts as a primer, and thus neither the synthesis of a polyA tail nor additional adaptors is required.

Also, according to another embodiment of the present invention, a small RNA detection sensor can be provided, wherein, by amplifying only a PCR-capable region consisting of only DNA, amplification is possible through a general PCR synthesis device, and the PCR-capable region includes a barcode region including information corresponding to the target small RNA, and thus the sequencing of an amplified product (amplicon) is possible without an additional library production process.

(a) to (e) of FIG. 2 are views for describing a method of amplifying small RNA using a small RNA detection sensor according to an embodiment of the present invention.

FIGS. 3A to 3D illustrate the nucleotide sequences of sensors according to an embodiment of the present invention and target small RNAs of the sensors (FIG. 3A: SEQ ID NO: 1; FIG. 3B: SEQ ID NO: 2; FIG. 3C: SEQ ID NO: 3; and FIG. 3D; SEQ ID NO: 4).

Figure 4A:
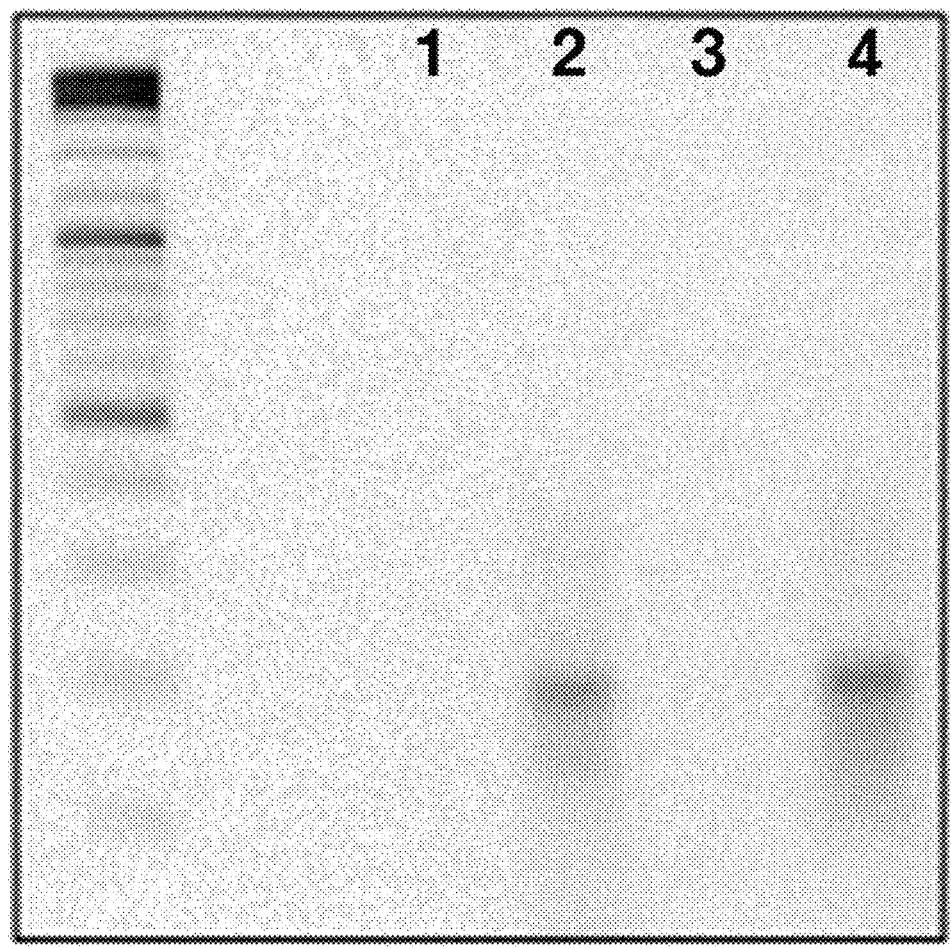
Figure 4B:
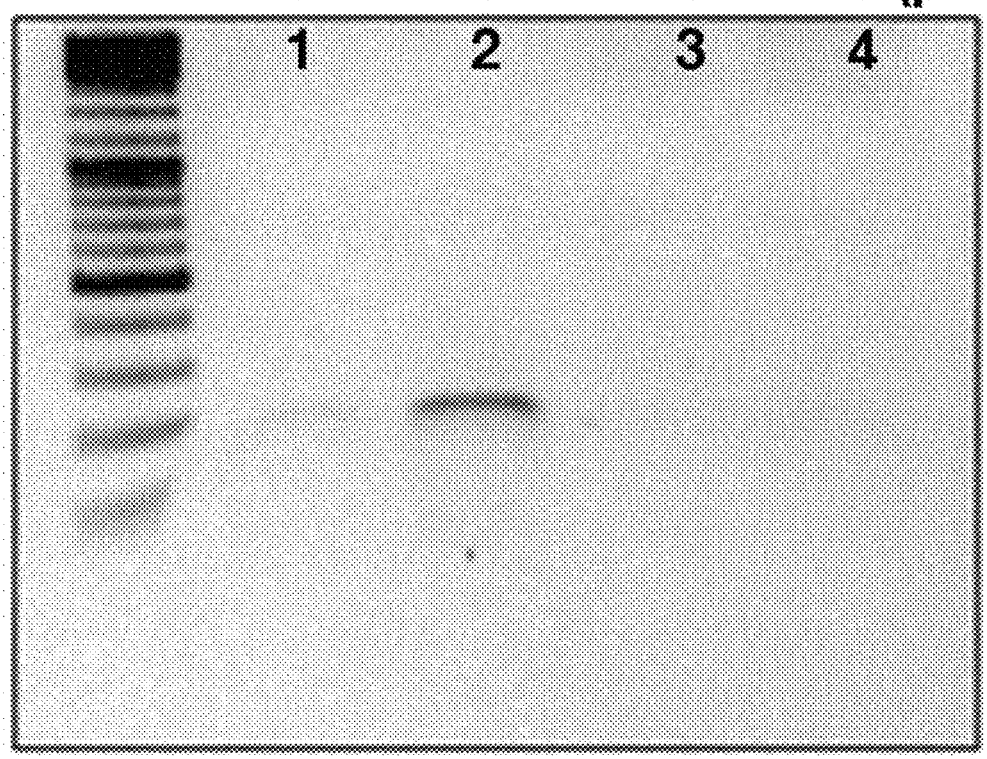

FIGS. 4A and 4B are images of general PCR results using sensors according to an embodiment of the present invention, after electrophoresis with 2% agarose gel.

Figure 5A:
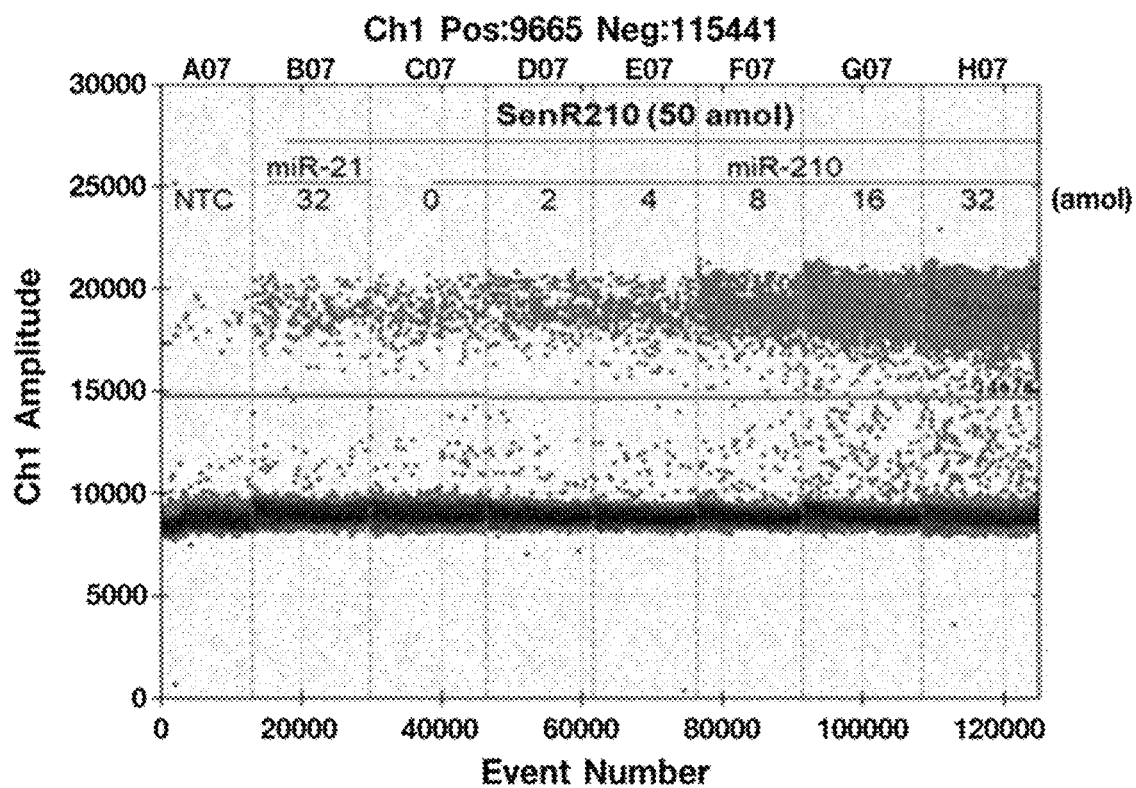
Figure 5B:
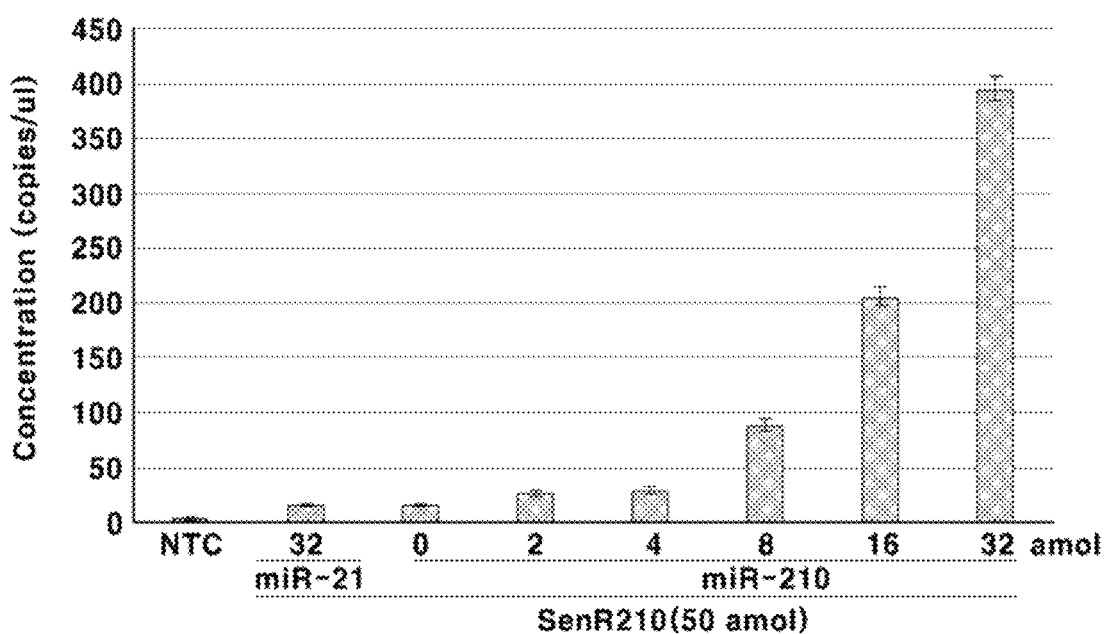

FIGS. 5A and 5B are graphs showing digital PCR results using sensors according to an embodiment of the present invention and the concentrations of detected small RNAs.

Figure 6A:
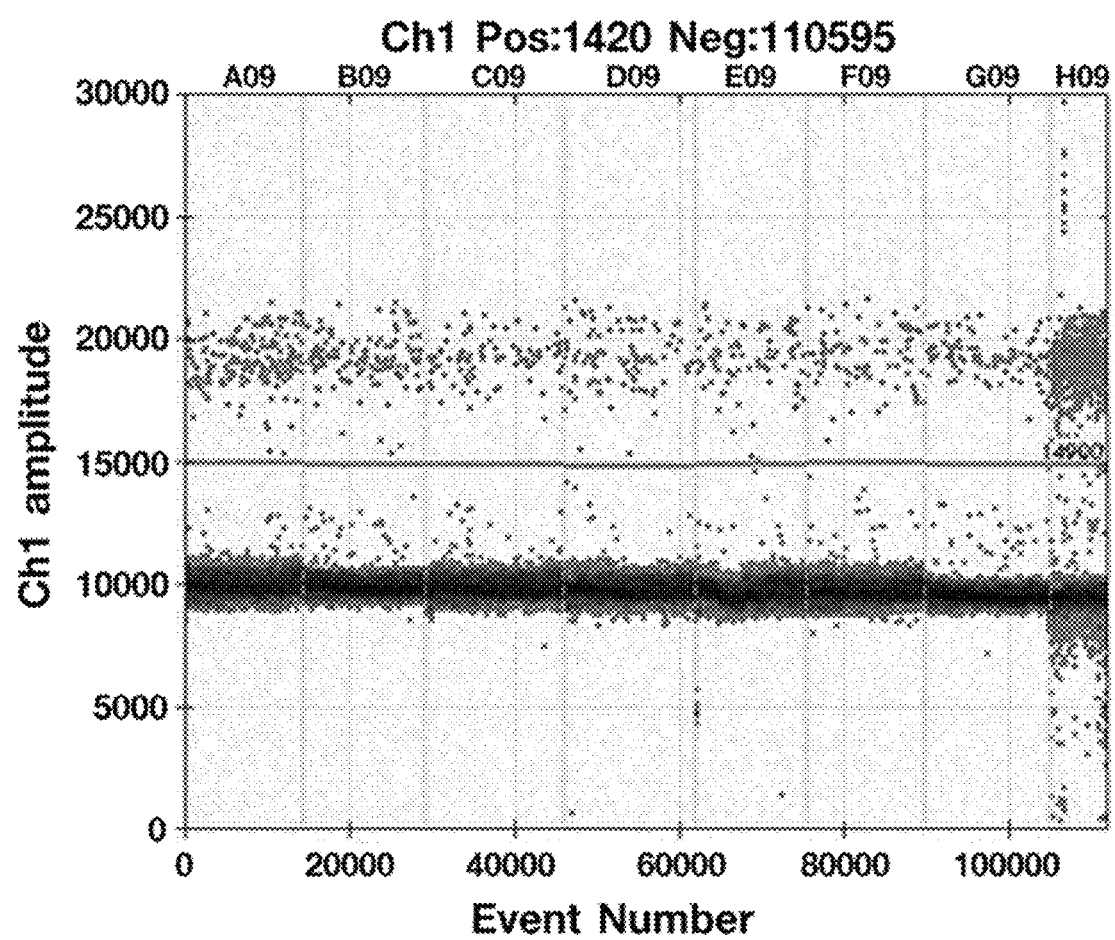
Figure 6B:
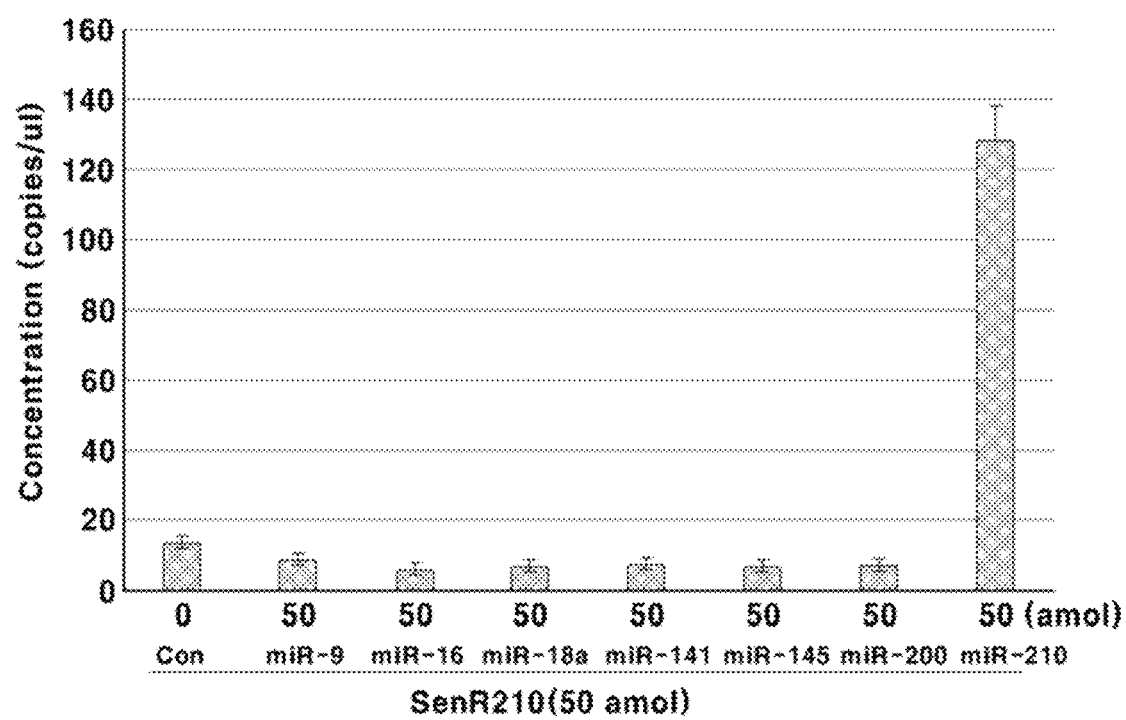

FIGS. 6A and 6B illustrate the results of measuring, by digital PCR the accuracy of sensors according to an embodiment of the present invention for target small RNA.

Figure 7:
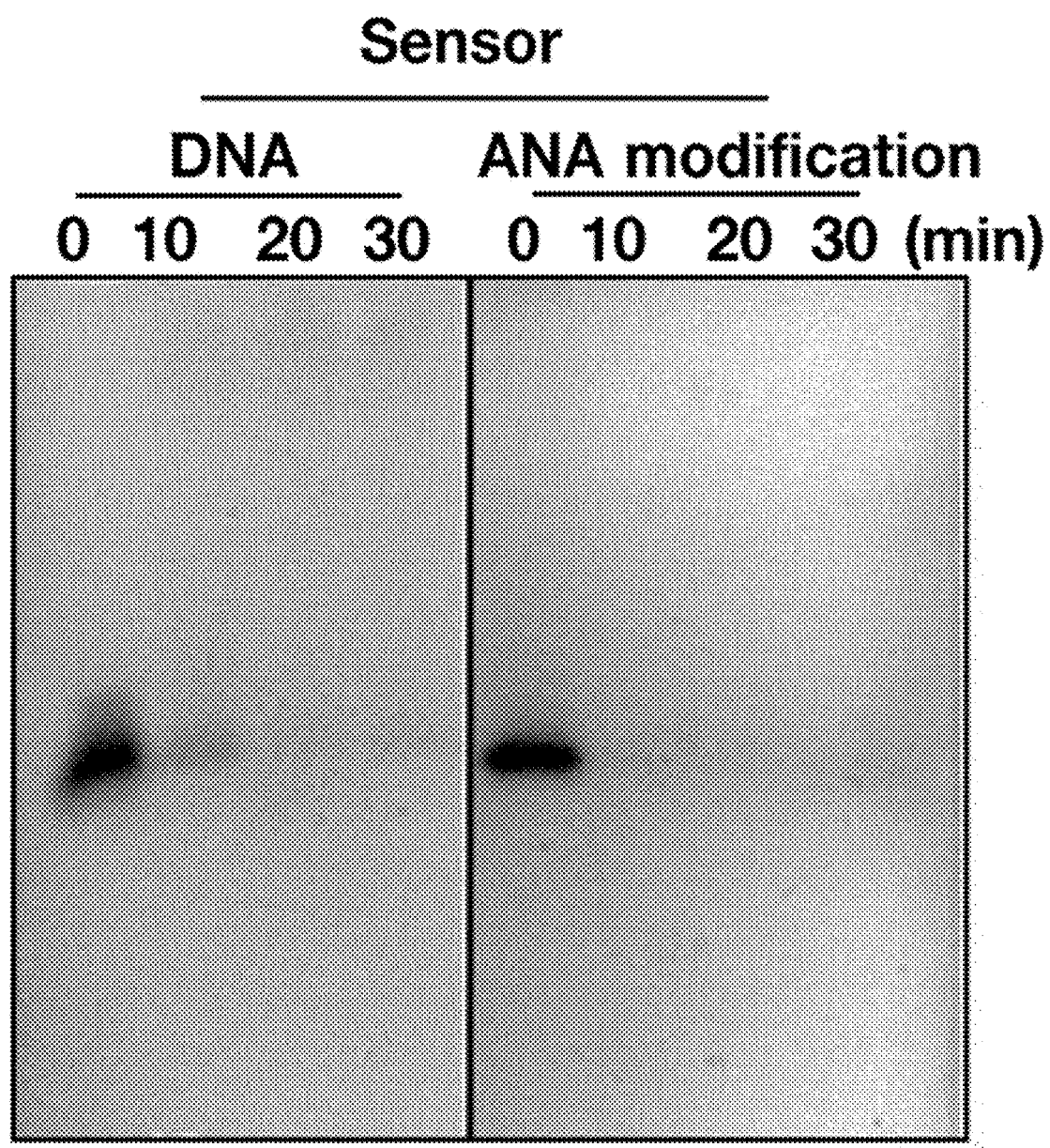

FIG. 7 illustrates gel electrophoresis images showing the ability of S1 nuclease to degrade a SenR210 DNA sensor, which is a small RNA detection sensor according to an embodiment of the present invention, and a small RNA detection sensor described in FIGS. 3A to 3D, in which some nucleotides were modified with ANA (ANA modification).

FIG. 8 illustrates the nucleotide sequence of the sensor SenR210rna (SEQ ID NO: 5) according to another embodiment of the present invention.

BEST MODE

Hereinafter, exemplary embodiments of the present invention will be described in detail with reference to the accompanying drawings.

Embodiments of the present invention are provided to more fully describe the present invention to those of ordinary skill in the art, and embodiments set forth herein may be changed into many different forms and are not intended to limit the scope of the present invention. Rather, these embodiments are provided so that the present invention will be thorough and complete, and will fully convey the scope of the present invention to those of ordinary skill in the art.

In addition, the thickness or size of each layer in the drawings can be exaggerated for convenience of explanation and clarity, and like reference numerals in the drawings denote like elements. As used herein, the term "and/or" includes any and all combinations of one or more of the associated listed items.

The terms used in the present specification are used to describe specific embodiments, and are not intended to limit the present invention. As used herein, the term "comprise" and/or "comprising" specify the presence of mentioned shapes, numbers, steps, operations, members, elements, and/or groups thereof, and do not preclude the presence or addition of at least one of other shapes, numbers, steps, operations, members, elements, and/or groups thereof.

Figure 1A:
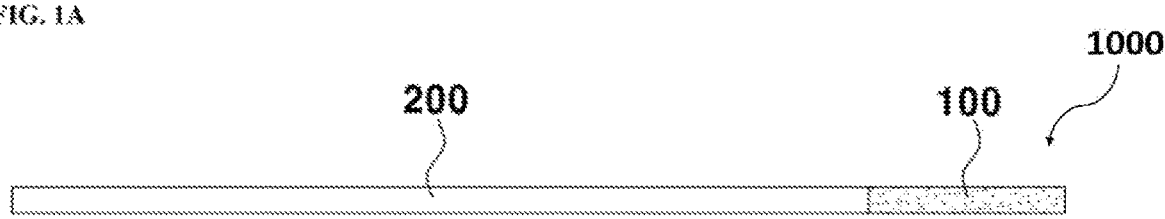
FIGS. 1A and 1B are schematic views for describing the structure of a small RNA detection sensor according to an embodiment of the present invention.
Figure 1B:
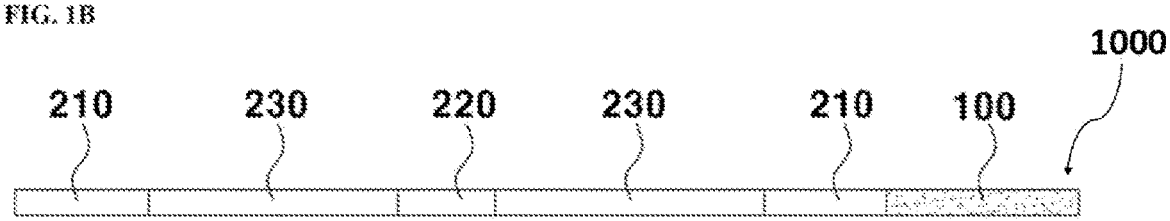

FIGS. 1A and 1B are schematic views for describing the structure of a small RNA detection sensor (1000) according to an embodiment of the present invention.

Referring to FIG. 1A, the small RNA detection sensor (1000) includes a first sensing region (100), which is bindable to small RNA, and a PCR-capable region 200 that is able to be amplified. The first sensing region 100 may include nucleotides having a sequence complementary to target small RNA, which is small RNA to be detected through the sensor 1000. In one embodiment, the nucleotides may be included at one end of the first sensing region 100. In addition, the nucleotides may be any one or more of DNA nucleotides, XNA nucleotides, ANA nucleotides, HNA nucleotides, INA nucleotides, and LNA nucleotides.

The small RNA may be a non-coding RNA molecule having a length of less than 200 nucleotides. For example, the small RNA may include microRNA (miRNA) and small interfering RNA (siRNA), but is not limited thereto, and any non-coding RNA and any small RNA that regulates a protein synthesis process may be used.

In one embodiment, the first sensing region 100 may further include an amine modification portion (not shown) at the 3' end thereof. The amine modification portion may completely eliminate the non-specific amplification of a sensor that may occur during the synthesis of replication region using the sensor 1000 and the amplification of the sensor 1000. For example, when a sensor 1000 without target small RNA hybridization is present in a test sample, the amine modification portion may prevent the sensor 1000 from self-amplifying. The amine modification portion may be at least one nucleotide with amine modification within the first sensing region 100 that is complementary to a target small RNA.

In one embodiment, at least one amine modification portion may be included in the first sensing region (100). The amine modification portion may be included at the 3' end of the first sensing region 100, and may be positioned in a plurality of regions including the 3' end of the first sensing region 100. The first sensing region 100 including the amine modification portion recognizes and binds to target small RNA, and even when a first sensing region of another small RNA detection sensor is recognized as target small RNA, PCR amplification due to the formation of a non-specific self-dimer may not proceed by an amine modification portion of the other small RNA detection sensor. Accordingly, the small RNA detection sensor with the amine modification portion, in compliance with an embodiment of the present invention, may enhance the detection and amplification sensitivity for its target small RNA.

In one embodiment, the first sensing region 100 may include a nucleotide substitution portion in which nucleotides of the first sensing region 100 are substituted with one or more different types of nucleotide analogs. The substitution with the nucleotide analog(s) may occur at a specific sequence position in the nucleotide sequence, and the substitution position may vary depending on the target RNA of the detection sensor, and may also be fixed regardless of target RNAs. The substituted nucleotide analog(s) may then be used to remove a sensor that does not bind to its target small RNA.

The PCR-capable region 200 may be coupled to the first sensing region 100 and is able to be amplified using a polymerase chain reaction (hereinafter, PCR). In one embodiment, one end of the PCR-capable region may be coupled to the first sensing region 100, and may consist of DNA nucleotides. In addition, the PCR-capable region 200 may further include information indicating a target small RNA to which the first sensing region 100 binds, which will be described below with reference to FIG. 1B.

FIG. 1B is a view for specifically describing the structure of a small RNA detection sensor according to an embodiment of the present invention. Referring to FIG. 1B, as described above with reference to FIG. 1A, the small RNA detection sensor 1000 includes the first sensing region 100 and the PCR-capable region 200, and the first sensing region 100 is the same as described above with reference to FIG. 1A.

The PCR-capable region 200 may include a primer binding region 210, a barcode region 220, and a residual nucleotide region 230. The primer binding region 210 may be located at one of both ends of the PCR-capable region 200, and since the PCR-capable region 200 consists of DNA nucleotides, a primer may bind to the primer binding region 210, thereby synthesizing a DNA double strand. In one embodiment, the nucleotide sequence of the primer binding region 210 may be constant regardless of whether the sensor performs sensing by varying the type of target small RNA to be probed or detected. Thus, it may be possible to amplify the sensor using a specific primer regardless of the type of target material.

The barcode region 220 may include information related to a target small RNA to which the first sensing region 100 binds. In one embodiment, the information may include any one or more selected from information indicating a protein, its expression is regulated by the target small RNA, information indicating a disease related to the target small RNA, and information indicating the nucleotide sequence of the target small RNA. Since the barcode region 220 includes information related to the target small RNA, the sensor 1000 is able to determine what the target small RNA sensed by the first sensing region 100 is even when only the PCR-capable region 200 is amplified, and may perform direct sequencing without an additional library construction process. The residual nucleotide regions 230 may be located at both sides of the barcode region 220, and as necessary, may further include an additional sensing portion (not shown) or a fluorescent portion (not shown).

FIG. 2 is a view for describing a method for detecting small RNA using a small RNA detection sensor according to an embodiment of the present invention.

Referring to FIG. 2, the sensor 1000 may be provided in a test sample including target small RNA (process a). The sensor 1000 may include: the first sensing region 100 including, at one end thereof, nucleotides having a sequence complementary to the target small RNA; and the PCR-capable region 200 that is coupled to the first sensing region 100. The target small RNA in the test sample may bind to the first sensing region 100 of the sensor (process b).

The sensor 1000 may synthesize the PCR-capable region 200 of the sensor 1000 using the bound target small RNA as a primer 300 to thereby produce a cDNA (process c). In this case, a strand 2000 complementary to the sensor 1000 may be a chimera type including the target small RNA 300 used as a primer and a replication region 400 synthesized corresponding to the PCR-capable region 200. Since the replication region 400 consists of DNA nucleotides, general PCR may be performed without an additional process of synthesizing cDNA from RNA.

In one embodiment, a process of performing priming binding, by the first sensing region 100, by recognizing the bound target small RNA as the primer 300 may be performed at 45° C. to 70° C., preferably at 50° C. to 65° C. When the temperature condition of the above process exceeds 70° C., the target small RNA may not bind to the first sensing region 100. When the priming binding process is performed at less than 45° C., a self-dimer may be formed by the first sensing region 100 of the sensors 1000 that are not bound target small RNAs, and thus non-specific strands are PCR-amplified, and consequently, desired results cannot be obtained. Since the first sensing region 100 has a nucleotide substitution portion, it is possible to perform binding by recognizing the target small RNA as a primer at the temperature ranging from 45° C. to 70° C.

After the replication region 400 is synthesized, the sensor 1000, the complementary strand 2000, the target small RNA 300, and a non-specific small RNA may be included in the test sample. In one embodiment, the single-stranded sensor 1000 without target binding and the non-specific small RNAs 300 may be selectively removed using a nuclease. As such, by removing RNA and the sensor, which are not amplification targets, before the amplification process, accurate detection for the target small RNA is enabled. In one embodiment, the nuclease may be included in a test sample for 15 minutes to 40 minutes to remove RNA and sensors that do not bind to the target small RNA, which are not amplification targets.

Such removal may be performed by binding between a substituted nucleotide analog of the first sensing region 100 and the nuclease. The nucleotide analog may include any one or more of arabino nucleic acid (ANA), locked nucleic acid (LNA), hexitol nucleic acid (HNA), glycol nucleic acid (GNA), and peptide nucleic acid (PNA), and preferably, may include arabino nucleic acid (ANA). The arabino nucleic acid (ANA) has high sensitivity to nucleases. Therefore, in one embodiment, when the arabino nucleic acid (ANA) of the small RNA detection sensor 1000 is exposed, the strand of the detection sensor 1000 may be cleaved by a nuclease. For example, when the first sensing region 100 binds to the target small RNA to thereby produce the replication region 400 complementary to the PCR-capable region 200, the test sample may include non-specific small RNAs that do not participate in binding, sensors that do not bind to the target small RNA, and sensors that bind to the target small RNA. In this case, when a nuclease is added to the test sample, the nuclease may recognize exposed arabino nucleic acid (ANA) in the non-bound small RNA detection sensor and selectively cleave the non-bound small RNA detection sensor.

As such, after removal of a non-bound detection sensor (non-bound miRNA sensor) with the substituted ANA, a nucleotide analog, and non-specific small RNA (background miRNA), the PCR amplification of detection sensor bound to the target small RNA is eligible, and thus accurate small RNA detection results can be provided even from sample amounts as small as picomoles and attomoles.

Subsequently, by using primers P1 and P2 specific to the primer binding region 210, PCR may be performed on the sensor 1000 and the chimera type strand 2000 complementary to the sensor 1000 (process d). DNA amplification is not performed on the entire region of the sensor 1000 and the complementary strand 2000, and DNA amplification may be performed on only the PCR-capable region 20 of the sensor 1000 and the replication region 400 except for the target small RNA 300 of the complementary strand 2000. That is, the target small RNA 300 and the first sensing region 100 having a nucleotide sequence complementary to the target small RNA are not amplified by the PCR technique. In one embodiment, since the first sensing region 100 includes an amine modification portion at the 3' end thereof, the non-specific amplification of sensors may be prevented.

An amplified product (e) may be a single strand consisting of the PCR-capable region 200 of the sensor and a single strand consisting of the replication region 400 synthesized from the PCR-capable region 200. In one embodiment, since the amplified intermediate and product do not include the target small RNA, amplification is possible by the PCR technique without a separate process, and sequencing may be performed using sequencing equipment without additional library production. In another embodiment, quantitative analysis may be performed on how many copies of the target small RNA are present in the test sample through digital PCR.

In addition, amplified products according to target small RNA may be distinguished by the barcode region 220 in the PCR-capable region 200, and thus HRM analysis may be directly performed without going through a separate process. In one embodiment, the sensor 1000 may also be applied to nanopore sequencing techniques by changing the PCR-capable region 200 of the sensor 1000, and target small RNA may be sequenced rapidly and conveniently using various DNA analysis and sequencing techniques without additional processes.

FIGS. 3A to 3D illustrate the nucleotide sequences of sensors according to an embodiment of the present invention and target small RNAs of the sensors. FIGS. 3A and 3B illustrate the nucleotide sequences of the sensors senR210 and senR21 for sensing and amplifying target small RNA 210 and target small RNA 21, and FIGS. 3C and 3D illustrate the nucleotide sequences of target small RNA 210 (miR-210) and target small RNA 21 (miR-21).

Referring to FIGS. 3A and 3B, the senR210 and senR21 sensors may be produced by substituting cytosine (C) at position $88^{th}$ nucleotide and position $138^{th}$ nucleotide, respectively, from the 5' end of the nucleotide sequence with an arabino nucleic acid (hereinafter, ANA), and may also be produced by substituting cytosine (C) at position $3^{rd}$ nucleotide from the 3' end of the nucleotide sequence with ANA. By producing the sensor through substitution of some cytosines with ANA, a nuclease may rapidly and accurately recognize and cleave the single-stranded small RNA detection sensor 1000 that has performed non-specific binding or does not bind to the target small RNA, or the specificity of the detection sensor 1000 for the target small RNA may be enhanced. In one embodiment, the substitution of cytosine at position 3 from the 3' end of the nucleotide sequence with ANA may enable the sensor 1000 to enhance specificity when recognizing the target small RNA 300.

In addition, the substitution of cytosines at position at position $88^{th}$ nucleotide and position $138^{th}$ nucleotide, respectively, from the 5' end of the nucleotide sequence of the senR210 and senR21 sensors with ANA may enhance efficiency in the process of removing the sensor 1000 that is not bound to the target small RNA 300 by using an enzyme. Among XNAs, ANA is very sensitive to S1 nuclease. Therefore, S1 nuclease is able to cleave, in the middle, a module of the sensor 1000 that has not be able to recognize the target small RNA 300 by the sensitivity of the substituted ANA, and thus may efficiently remove the sensor 1000 that is not bound to the target small RNA 3), and accordingly, may prevent the sensor 1000 from self-amplifying or being non-specifically amplified. In addition, since the single-stranded detection sensor that is not bound to the target small RNA is effectively removed by the substituted ANA, the amplification of noise unrelated to the target small RNA may be prevented in the subsequent PCR amplification process, and accordingly, target small RNAs may be accurately detected.

FIGS. 4A and 4B are images of general PCR results using sensors according to an embodiment of the present invention. By using the small RNA detection sensors (Sen R210 and Sen R21) according to an embodiment of the present invention as described above with reference to FIGS. 1A, 1B, and 3A to 3D, an amplified product obtained by amplifying the PCR-capable region 200 and the replication region 400 using the amplification method as illustrated in FIG. 2 was confirmed as follows.

The concentration of each of SenR210 and SenR21, which are sensors described above with reference to FIGS. 3A and 3B is fixed at 50 pmol, each of target small RNAs (miR-210 and miR-21) is added to a tube, and then cDNA is synthesized using Therminator DNA polymerase for about 10 minutes. After the synthesis of cDNA, a nuclease that degrades single-stranded DNA and RNA is used for treatment. Subsequently, amplification may be performed using primer sets specific to the primer binding region 210 of the PCR-capable region 200. Referring to FIG. 4A, amplified products (amplicons) can be confirmed only in lanes 2 and 4, which indicates that the SenR210 and SenR21 sensors specifically amplify only miR-210 and miR-21, respectively, which are target small RNAs.

In addition, the concentration of SenR210, which is a small RNA detection sensor, is fixed at 5 pmol, miR-210, which is target small RNA, is added at a concentration of 1.5 pmol, and then an experiment is performed under the same conditions as described above. Referring to FIG. 4B, amplified products (amplicons) can be confirmed only in lanes 1 and 2, which indicates that the SenR210 sensor operates in accordance with the concentration of the target small RNA (miR-210). In addition, to confirm the accurate binding of the sensor, another small RNA (miR-21), which is not the target small RNA of the sensor, is injected into the test sample together with the sensor (lane 3), and as a result, no presence of an amplicon can be confirmed, which indicates that SenR210, which is a sensor according to an embodiment of the present invention, accurately operates in a manner specific to the nucleotide sequence.

FIGS. 5A and 5B are graphs showing digital PCR results using sensors according to an embodiment of the present invention and the concentrations of detected small RNAs.

To examine the sensitivity and accuracy of the sensor according to the concentration of target small RNA, an experiment was performed as follows. First, 50 amol of the SenS210 sensor and various concentrations, i.e., 0, 2, 4, 8, 16, and 32 amol, of miR-210, which is target small RNA in this experiment, are added to a tube, and distilled water is added thereto so that the total amount becomes 10 μm. In addition, 2 μl of a reaction buffer (200 mM Tris-HCl, 100 mM (NH$_4$)$_2$SO$_4$, 100 mM KCl, 20 mM MgSO$_4$, 1% Triton X-100, (pH 8.8 at 25° C.)) is added, and then the resultant mixture is heated at 95° C. for 30 minutes, followed by incubation at 52° C. for 10 minutes.

Subsequently, 2 units of a Therminator DNA polymerase mixture is added in a state where incubation at 52° C. is maintained, and after spinning down, incubation is performed at 52° C. for 2 minutes and at 72° C. for 2 minutes. After the temperature of the PCR is lowered to 37° C., an S1 nuclease mixture (74 mM sodium acetate (pH 4.5 at 25° C.), 555 mM NaCl and 3.7 mM ZnSO$_4$, 200 units of S1 nuclease) is added and incubation is further performed for 45 minutes. Then, the temperature of a PCR block is raised to 70° C., the nuclease is thermally inactivated for 20 minutes, and then the reaction sample is purified using a nucleotide removal kit. The eluted sample is diluted 1/2000 to perform digital PCR.

Thereafter, the concentration of SenR210, which is a sensor according to an embodiment of the present invention, is fixed at 50 amol, and then miR-210, which is target small RNA, is added at concentrations of 0, 2, 4, 8, 16, or 32 amol (lanes 3 to 7), and as controls, miR-21 is added at a concentration of 32 amol (lane 2) or small RNA is not added (lane 1), and cDNA is synthesized using Therminator DNA polymerase, which is a DNA polymerase. Then, a single-stranded specific nuclease is added to remove non-bound single-stranded sensors, and then digital PCR is performed. Referring to FIG. 5A, from the concentration of target miR-210 of 4 amol or more, the target small RNA detection of SenR210 can be confirmed. It can also be confirmed that lane 2, which is the case of adding 32 amol of miR-21, which is non-target small RNA, exhibits a fluorescence value similar to that of lane 1, which is a sample in which RNA is not added. This suggests that the sensor 1000 according to an embodiment of the present invention accurately operates even at the amol level in a manner specific only to the target small RNA.

Referring to FIG. 5B, in the graph, the y axis denotes a fluorescence value calculated for total droplets, which means the number of copies of miR-210 detected per microliter. According to the graph, it can be seen that the fluorescence value increases according to the concentration of miR-210, which is target small RNA, in the test sample, and as shown in Table 1 below, it was confirmed that, when miR-210 is added to the test sample at a concentration ranging from 0 amol to 32 amol, the numbers of copies of miR-210 are 26, 28, 88, 206, and 395, respectively, per 1 microliter

TABLE 1

| Sample | copy/ μl | copy/ 20 μl | PoissonConf Max | PoissonConf Min | Positive | Negative | Number of droplets |
|---|---|---|---|---|---|---|---|
| NTC | 2 | 40 | 3 | 1 | 23 | 13,267 | 13,290 |
| miR-21 32 amol | 15 | 304 | 17 | 13 | 215 | 16,575 | 16,790 |
| miR-210 0 amol | 17 | 336 | 19 | 15 | 235 | 16,300 | 16,535 |
| miR-210 2 amol | 26 | 512 | 28 | 23 | 329 | 14,976 | 15,305 |
| miR-210 4 amol | 28 | 562 | 31 | 25 | 348 | 14,416 | 14,764 |
| miR-210 8 amol | 88 | 1,760 | 94 | 83 | 1,088 | 13,946 | 15,034 |
| miR-210 16 amol | 206 | 4,120 | 214 | 198 | 2,709 | 14,150 | 16,859 |
| miR-210 32 amol | 395 | 7,900 | 407 | 384 | 4,718 | 11,811 | 16,529 |

Digital PCR is a technique that can measure the copy number of target gene expression by making 20 μl of a sample into about 1 nl of small droplets, and with the existing gene expression detection technology, it is impossible to detect a gene material in amol units in a biological sample. As such, the amplification sensor and method according to an embodiment of the present invention enables detection of the concentration of target small RNA included in: single cells; single organelles such as nuclei, mitochondria, chloroplasts, and ERs; or a droplet of blood.

FIGS. 6A and 6B illustrate the results of measuring the accuracy of sensors according to an embodiment of the present invention for target small RNA.

To confirm the detection accuracy of the sensor produced according to an embodiment of the present invention for target small RNA, the following experiment is performed. First, 50 amol of SenR210, which is a sensor specific to miR-210 as target small RNA, and 32 amol of each of various types of small RNAs, i.e., miR-16, miR-18a, miR-141, miR-145, miR-200, and miR-210, are added to a PCR tube, and then distilled water is added thereto to a total volume of 10 μl. In addition, 2 μl of a reaction buffer (200 mM Tris-HCl, 100 mM (NH$_4$)$_2$SO$_4$, 100 mM KCl, 20 mM MgSO$_4$, 1% Triton X-100, (pH 8.8 at 25° C.)) is added, and then the resultant mixture is heated at 95° C. for 30 minutes, followed by incubation at 52° C. for 10 minutes. Thereafter, 2 units of a Therminator DNA polymerase mixture is added in a state where incubation at 52° C. is maintained, and after spinning down, incubation is performed at 52° C. for 2 minutes and at 72° C. for 2 minutes. After the temperature of the PCR is lowered to 37° C., an S1 nuclease mixture (74 mM sodium acetate (pH 4.5 at 25° C.), 555 mM NaCl and 3.7 mM ZnSO$_4$, 200 units of S1 nuclease) is added and incubation is further performed for 45 minutes. Then, the temperature of a PCR block is raised to 70° C., the nuclease is thermally inactivated for 20 minutes, and then the reaction sample is purified using a nucleotide removal kit. The eluted sample is diluted 1/2000 to perform digital PCR.

Thereafter, the SenR210 sensor according to an embodiment of the present invention is fixed at a concentration of 50 amol, and then no small RNA is added to lane A09, and 32 amol of miR-9, miR-16, miR-18a, miR-141, miR-145, miR-200, and miR-210 are respectively added to lanes B09 to H09, followed by cDNA synthesis using Therminator DNA polymerase. Then, single-stranded DNA that is not bound to the target small RNA and RNA that is not bound to single-stranded DNA are cleaved using a single-stranded specific nuclease.

Referring to FIG. 6A, it can be confirmed that the SenR210 sensor accurately detects RNA only in lane H09 including miR-210, which is target small RNA. It can also be confirmed that the SenR210 sensor does not operate in the other lanes that exclude small RNA or contain miRNAs having six different types of nucleotide sequences other than the target small RNA, from which it can be confirmed that the sensor according to an embodiment of the present invention operates in a target small RNA-specific manner.

Referring to FIG. 6B, the y axis denotes a fluorescence value calculated for total droplets, which means the number of copies of miRNA detected per microliter. According to the graph, it can be seen that, only when miR-210, which is target small RNA, is added to the test sample, the fluorescence value is increased, and it can be confirmed that, when the other miRNAs, i.e., miR-9, miR-16, miR-141, miR-145, and miR-200, are added, no increase in the fluorescence value is shown, i.e., the SenR210 sensor does not operate.

FIG. 7 illustrates gel electrophoresis images showing the ability of S1 nuclease to degrade a SenR210 DNA sensor, which is a small RNA detection sensor according to an embodiment of the present invention, and a small RNA detection sensor described in FIGS. 3A to 3D, in which some nucleotides were modified with ANA (ANA modification).

For the SenR210 DNA sensor and the ANA modification sensor. S1 nuclease is added to the sample and incubated at 37° C. for 10 minutes, 20 minutes, and 30 minutes, followed by gel loading to confirm the results. Referring to FIG. 7, it can be seen that the sensor with ANA modification is rapidly degraded by S1 nuclease compared to the DNA sensor. Thus, it is preferable that some nucleotides of the small RNA detection sensor according to an embodiment of the present invention are substituted with ANA in order to remove non-specific amplification.

FIG. 8 illustrates the nucleotide sequence of a SenR210rna sensor according to another embodiment of the present invention. FIG. K illustrates the nucleotide sequence of SenR210rna for sensing and amplifying target small RNA 210.

Referring to FIG. 8, the SenR210rna sensor may be produced by substituting, with RNA, DNA nucleotides at positions 24, 25, 26, 93, 94, 95, and 140 from the 5' end of the small RNA detection sensor described above with reference to FIG. 3A. The sensor having the DNA nucleotides substituted with RNA binds to primers for module amplification, but the RNA is not amplified by taq polymerase. Thus, only a DNA replication region (400 of FIG. 2) synthesized using miR-210, which is target small RNA, as a primer and SenR210rna, which is a sensor with some DNA nucleotides substituted with RNA, as a template may be specifically amplified. In addition, during the substitution with RNA, the substitution of a DNA nucleotide at position 140 of SenR210rna with RNA is to prevent abnormal PCR amplification due to non-specific binding of the sensor.

In addition, the nucleotide substitution portion of the SenR210rna sensor may further include a nucleotide substitution portion with an ANA nucleotide, in addition to the RNA nucleotide. As described above with reference to FIGS. 1 to 7, the ANA nucleotides in a single-stranded detection sensor that is not bound to the target small RNA may be exposed to a nuclease, so that the single-stranded detection sensor can be removed.

The foregoing description of the present invention is not limited to the aforementioned embodiments and the accompanying drawings, and it will be obvious to those of ordinary skill in the art to which the present invention pertains that the invention may be substituted, modified, and changed into many different forms without departing from the technical spirit of the present invention.

The invention claimed is:

1. A small RNA detection method comprising:
providing a sensor comprising: at one end thereof, a first sensing region comprising nucleotides having a sequence complementary to a target small RNA and a PCR-capable region that is coupled to the first sensing region, wherein the first sensing region comprises at least one amine modification portion and at least one nucleotide substitution portion comprising an ANA nucleotide, and the PCR-capable region comprises primer-binding regions, a barcode region, and a residual nucleotide region;
allowing the target small RNA in a test sample to bind to the first sensing region of the sensor;
synthesizing a replication region by replicating the PCR-capable region using the bound target small RNA as a primer to form a chimera strand complementary to the sensor;
adding a nuclease to the test sample, wherein the nuclease cleaves non-specific small RNA that has not bound to the first sensing region and cleaves the first sensing region that has not formed a chimera with the target small RNA;
removing the cleaved sensor and non-specific small RNAs; and
PCR amplifying the PCR-capable region and the replication region using a set of primers specific to the primer-binding regions of the sensor and primer-binding regions of the chimera strand.

2. The small RNA detection method of claim 1, wherein the binding of the target small RNA to the first sensing region is performed at 45° C. to 70° C.

3. The small RNA detection method of claim 1, wherein a nucleotide substitution portion comprising an ANA nucleotide is located at each of the $88^{th}$ and $138^{th}$ nucleotides from the 5' end of the sensor.

4. The small RNA detection method of claim 1, wherein the target small RNA is microRNA or small interfering RNA.

5. The small RNA detection method of claim 1, wherein the barcode region consists of 9 nucleotides.

* * * * *

SEQUENCE LISTING

```
<160> NUMBER OF SEQ ID NOS: 5

<210> SEQ ID NO 1
<211> LENGTH: 143
<212> TYPE: DNA
<213> ORGANISM: Artificial Sequence
<220> FEATURE:
<223> OTHER INFORMATION: SenR210

<400> SEQUENCE: 1
aatgatacgg cgaccaccga gatctacacg ttcagagttc tacagtccga cgatctggaa     60
ttctcgggtg ccaaggaact ccagtcaara catcacgatc tcgtatgccg tcttctgctt    120
gtcagccgct gtcacacgca cag                                            143

<210> SEQ ID NO 2
<211> LENGTH: 143
<212> TYPE: DNA
<213> ORGANISM: Artificial Sequence
<220> FEATURE:
<223> OTHER INFORMATION: SenR21

<400> SEQUENCE: 2
aatgatacgg cgaccaccga gatctacacg ttcagagttc tacagtccga cgatctggaa     60
ttctcgggtg ccaaggaact ccagtcaara ccgtgatatc tcgtatgccg tcttctgctt    120
```

```
gtcaacatca gtctgataag cta                                          143

<210> SEQ ID NO 3
<211> LENGTH: 22
<212> TYPE: RNA
<213> ORGANISM: Artificial Sequence
<220> FEATURE:
<223> OTHER INFORMATION: hsa-miR-210-3p

<400> SEQUENCE: 3
cugugcgugu gacagcggcu ga                                            22

<210> SEQ ID NO 4
<211> LENGTH: 22
<212> TYPE: RNA
<213> ORGANISM: Artificial Sequence
<220> FEATURE:
<223> OTHER INFORMATION: hsa-miR-21-5p

<400> SEQUENCE: 4
uagcuuauca gacugauguu ga                                            22

<210> SEQ ID NO 5
<211> LENGTH: 149
<212> TYPE: DNA
<213> ORGANISM: Artificial Sequence
<220> FEATURE:
<223> OTHER INFORMATION: SenR210rna

<400> SEQUENCE: 5
aatgatacgg cgaccaccga gatrcrtrac acgttcagag ttctacagtc cgacgatctg    60
gaattctcgg gtgccaagga actccagtca aracatcarc rgratctcgt atgccgtctt   120
ctgcttgtca gccgctgtca cacgcacag                                    149
```